US011771410B2

(12) United States Patent
Morin et al.

(10) Patent No.: US 11,771,410 B2
(45) Date of Patent: Oct. 3, 2023

(54) DEVICES AND METHODS FOR THE TREATMENT OF VASCULAR ABNORMALITIES

(71) Applicant: St. Jude Medical, Cardiology Division, Inc., St. Paul, MN (US)

(72) Inventors: Kristen Morin, St. Paul, MN (US); Trevor Springer, Stillwater, MN (US); Andrey Samaray, Champlin, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 88 days.

(21) Appl. No.: 17/391,666

(22) Filed: Aug. 2, 2021

(65) Prior Publication Data
US 2022/0031295 A1 Feb. 3, 2022

Related U.S. Application Data

(60) Provisional application No. 63/060,221, filed on Aug. 3, 2020.

(51) Int. Cl.
*A61B 17/00* (2006.01)
*A61B 17/12* (2006.01)

(52) U.S. Cl.
CPC .... *A61B 17/0057* (2013.01); *A61B 17/12122* (2013.01); *A61B 2017/00592* (2013.01); *A61B 2017/00623* (2013.01); *A61B 2017/00628* (2013.01); *A61B 2017/00632* (2013.01); *A61B 2017/00871* (2013.01)

(58) Field of Classification Search
CPC .......... A61B 17/0057; A61B 17/12122; A61B 2017/00592; A61B 2017/00623; A61B 2017/00628; A61B 2017/00632; A61B 2017/00871
See application file for complete search history.

(56) References Cited

U.S. PATENT DOCUMENTS

| | | |
|---|---|---|
| 2009/0209855 A1 | 8/2009 | Drilling et al. |
| 2012/0271337 A1* | 10/2012 | Figulla ............. A61B 17/12168 87/9 |
| 2012/0323267 A1* | 12/2012 | Ren ................... A61B 17/12122 606/191 |
| 2017/0014113 A1* | 1/2017 | Ma .................... A61B 17/12177 |
| 2017/0095256 A1 | 4/2017 | Lindgren et al. |
| 2019/0110796 A1* | 4/2019 | Jayaraman ....... A61B 17/12168 |
| 2019/0274668 A1 | 9/2019 | Glimsdale et al. |
| 2020/0085445 A1 | 3/2020 | Wang et al. |
| 2020/0178981 A1 | 6/2020 | Anderson et al. |

FOREIGN PATENT DOCUMENTS

CN 104856741 A 8/2015

OTHER PUBLICATIONS

Extended European Search Report for EP Patent Application No. 21189037.1, dated Jan. 4, 2022, 21 pages.

* cited by examiner

*Primary Examiner* — Alexander J Orkin
(74) *Attorney, Agent, or Firm* — Armstrong Teasdale LLP

(57) ABSTRACT

Described herein is a medical device for treating a target site. The medical device includes a proximal end including a disc and a distal end including a lobe. The disc and lobe are connected by a connecting member. The disc includes a proximal surface, a distal surface, and a central surface extending between and connecting the proximal surface and distal surface, wherein the central surface separates the proximal surface from the distal surface by a predetermined depth distance.

16 Claims, 7 Drawing Sheets

DEVICES AND METHODS FOR THE TREATMENT OF VASCULAR ABNORMALITIES

CROSS-REFERENCE TO RELATED APPLICATIONS

This application claims the benefit of priority to U.S. Provisional Patent Application No. 63/060,221, filed Aug. 3, 2020, the entire contents of which are hereby incorporated by reference herein.

BACKGROUND OF THE DISCLOSURE

A. Field of Disclosure

The present disclosure relates generally to medical devices that are used in the human body. In particular, the present disclosure is directed to embodiments of an occlusion device that enables material apposition against tissue walls surrounding a vascular abnormality and facilitates a smooth transition between the tissue and the device. More specifically, the present disclosure is directed to an occlusion device with a disc having an increased depth, giving the disc a more three-dimensional cross-section. The embodiments and methods disclosed herein enable improved blood flow along or proximate to the disc after the occlusion device has been placed within the target site.

B. Background

An occluder is a medical device used to treat (e.g., occlude) tissue at a target site within the human body, such as an abnormality, a vessel, an organ, an opening, a chamber, a channel, a hole, a cavity, a lumen, or the like. For example, an occluder may be used in Left Atrial Appendage (LAA) closures. LAAs are common heart defects in which there is a sac in the muscle wall of the left atrium. When a patient experiences atrial fibrillation (AFib), a blood clot may be formed in the LAA which may become dislodged and enter the blood stream. By occluding the LAA, the release of blood clots from the LAA may be significantly reduced, if not eliminated. Various techniques have been developed to occlude the LAA. For instance, balloon-like devices have been developed that are configured to be implanted completely within the cavity of the LAA, while surgical techniques have also been developed where the cavity of the LAA is inverted and surgically closed.

In the case of some known medical devices, a lobed portion of the device sits in a body of the LAA, and a disc portion is engaged with the opening of the LAA. The disc of these known devices is generally a two-dimensional shape, formed from two directly adjacent layers of metal fabric. With the diverse anatomy of LAAs, the implantation of a medical device designed to occlude the LAA may not result in optimal implantation, and the two-dimensional disc of the above described medical devices may potentially slip at least partially into the opening of the LAA, which may lead to areas of stagnant blood flow within the patient's vascular system. The presence of stagnant blood flow may increase the risk of a patient developing device related thrombosis (DRT), which may lead to further medical complications.

It would be advantageous to provide an improved occlusion device that reduces the risk of DRT by minimizing stagnant blood flow proximate to the deployed medical device.

SUMMARY OF THE DISCLOSURE

The present disclosure generally relates to medical devices and methods of use thereof, including a disc with increased depth, giving the disc a more three-dimensional cross section which facilitates improved blood flow along or proximate to the disc after the occlusion device has been placed within the target site.

In one embodiment, the present disclosure is directed to a medical device for treating a target site. The medical device includes a proximal end and a distal end. The proximal end includes a disc and the distal end includes a lobe. The disc and the lobe are connected by a connecting member. The disc includes a proximal surface, a distal surface, and a central surface. The central surface extends between and connects the proximal surface and the distal surface. The central surface separates the proximal surface from the distal surface by a predetermined depth distance.

In another embodiment, a delivery system for deploying a medical device to a target site is provided. The delivery system includes a medical device and a delivery device. The medical device includes a proximal end and a distal end. The proximal end includes a disc and the distal end includes a lobe. The disc and the lobe are connected by a connecting member. The disc includes a proximal surface, a distal surface, and a central surface. The central surface extends between and connects the proximal surface and the distal surface. The central surface separates the proximal surface from the distal surface by a predetermined depth distance. The delivery device includes a delivery catheter, a delivery cable within the delivery catheter and translatable with respect to the delivery catheter, and a coupling member configured to couple the medical device to the delivery cable for facilitating at least one of deployment of the medical device at the target site and subsequent removal of the frame from the medical device.

In a further embodiment, a method for occluding a Left Atrial Appendage is provided. The method includes providing a medical device. The medical device includes a proximal end and a distal end. The proximal end includes a disc and the distal end includes a lobe. The disc and the lobe are connected by a connecting member. The disc includes a proximal surface, a distal surface, and a central surface. The central surface extends between and connects the proximal surface and the distal surface. The central surface separates the proximal surface from the distal surface by a predetermined depth distance. The method also includes advancing the medical device to the LAA using the delivery system, positioning the medical device relative to the LAA to occlude blood flow, and de-coupling the medical device from the delivery cable to deploy the medical device.

BRIEF DESCRIPTION OF THE DRAWINGS

Corresponding reference characters indicate corresponding parts throughout the several views of the drawings. It is understood that that Figures are not necessarily to scale.

DETAILED DESCRIPTION OF THE DISCLOSURE

Figure 1:
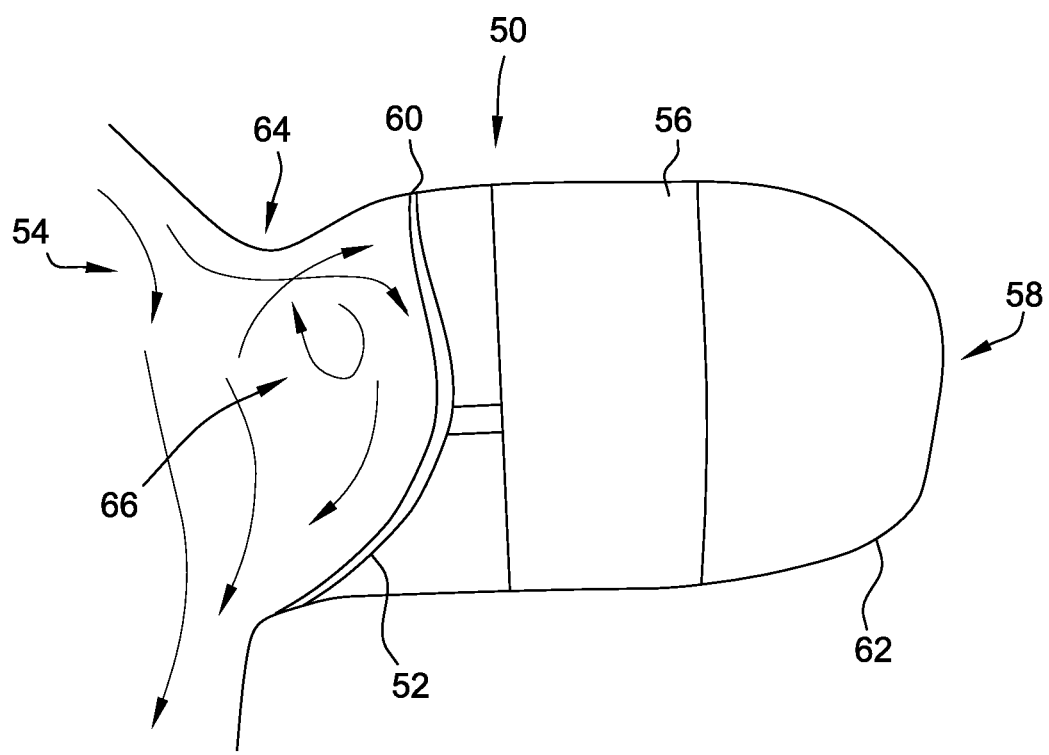
FIG. 1 is a schematic diagram of blood flow along or proximate to a known medical device, when the medical device is deployed at a target site.

The present disclosure relates generally to medical devices that are used in the human body. Specifically, the present disclosure provides medical devices, such as occlusion devices, including a distal lobe and a proximal disc, in which the disc has a defined depth, or a more three-dimensional shape than two-dimensional discs of at least some known medical devices.

Accordingly, the occlusion devices of the present disclosure facilitate improved and more uniform apposition of the disc against the tissue surrounding the vascular abnormality, which enables a smooth transition between the surrounding tissue and the medical device. Therefore, stagnant blood flow around the medical device or the abnormality may be reduced or eliminated.

The disclosed embodiments may lead to more consistent and improved patient outcomes. It is contemplated, however, that the described features and methods of the present disclosure as described herein may be incorporated into any number of systems as would be appreciated by one of ordinary skill in the art based on the disclosure herein.

Although the exemplary embodiment of the medical device is described as treating a target site including a left atrial appendage (LAA), it is understood that the use of the term "target site" is not meant to be limiting, as the medical device may be configured to treat any target site, such as an abnormality, a vessel, an organ, an opening, a chamber, a channel, a hole, a cavity, or the like, located anywhere in the body. The term "vascular abnormality," as used herein is not meant to be limiting, as the medical device may be configured to bridge or otherwise support a variety of vascular abnormalities. For example, the vascular abnormality could be any abnormality that affects the shape of the native lumen, such as an atrial septal defect, an LAA, a lesion, a vessel dissection, or a tumor. Embodiments of the medical device may be useful, for example, for occluding an LAA, patent foreman ovalis (PFO), atrial septal defect (ASD), ventricular septal defect (VSD), or patent ductus arteriosus (PDA), as noted above. Furthermore, the term "lumen" is also not meant to be limiting, as the vascular abnormality may reside in a variety of locations within the vasculature, such as a vessel, an artery, a vein, a passageway, an organ, a cavity, or the like. As used herein, the term "proximal" refers to a part of the medical device or the delivery device that is closest to the operator, and the term "distal" refers to a part of the medical device or the delivery device that is farther from the operator at any given time as the medical device is being delivered through the delivery device. In addition, the terms "deployed" and "implanted" may be used interchangeably herein.

Some embodiments of the present disclosure provide an improved percutaneous catheter directed intravascular occlusion device for use in the vasculature in patients' bodies, such as blood vessels, channels, lumens, a hole through tissue, cavities, and the like, such as a left atrial appendage. Other physiologic conditions in the body occur where it is also desirous to occlude a vessel or other passageway to prevent blood flow into or therethrough. These device embodiments may be used anywhere in the vasculature where the anatomical conditions are appropriate for the design.

The medical device may include one or more layers of occlusive material, wherein each layer may be comprised of any material that is configured to substantially preclude or occlude the flow of blood so as to facilitate thrombosis. As used herein, "substantially preclude or occlude flow" shall mean, functionally, that blood flow may occur for a short time, but that the body's clotting mechanism or protein or other body deposits on the occlusive material results in occlusion or flow stoppage after this initial period.

The present disclosure now will be described more fully hereinafter with reference to the accompanying drawings, in which some, but not all embodiments of the disclosure are shown. Indeed, this disclosure may be embodied in many different forms and should not be construed as limited to the embodiments set forth herein; rather, these embodiments are provided so that this disclosure will satisfy applicable legal requirements. Like numbers refer to like elements throughout.

As shown in FIG. 1, at least some conventional or known medical devices 50 used for the occlusion of abnormalities include a disc 52 at a proximal end 54 and a lobe 56 at a distal end 58 thereof. Disc 52 is formed from an occlusive material that extends in a flat (e.g., two-dimensional) and planar configuration from a center of medical device 50 to a peripheral edge 60.

When known medical device 50 is deployed at a target site 62 (e.g., a left atrial appendage (LAA)), lobe 56 is positioned within the body of the LAA 62 and provides a layer of occlusion. Disc 52 is intended to abut the tissue at an opening 64 of the LAA and provides another layer of occlusion. Additionally, disc 52 prevents lobe 56 from shifting within the body of the LAA 62. When disc 52 has a two-dimensional configuration, disc 52 may recede at least partially into the body of the LAA 62, which may lead to areas 66 of stagnant flow in the region between opening 64 and the retracted edge 60 of disc 52, thereby increasing the risk of the patient developing DRT.

The medical devices of the present disclosure include a disc having a more three-dimensional shape, providing more depth and allowing for greater material apposition against the tissue at the opening to the abnormality while allowing for a smooth transition between the surrounding tissue and the medical device. The medical devices of the present disclosure thereby minimize the above-described disadvantages of known medical devices.

Figure 2:
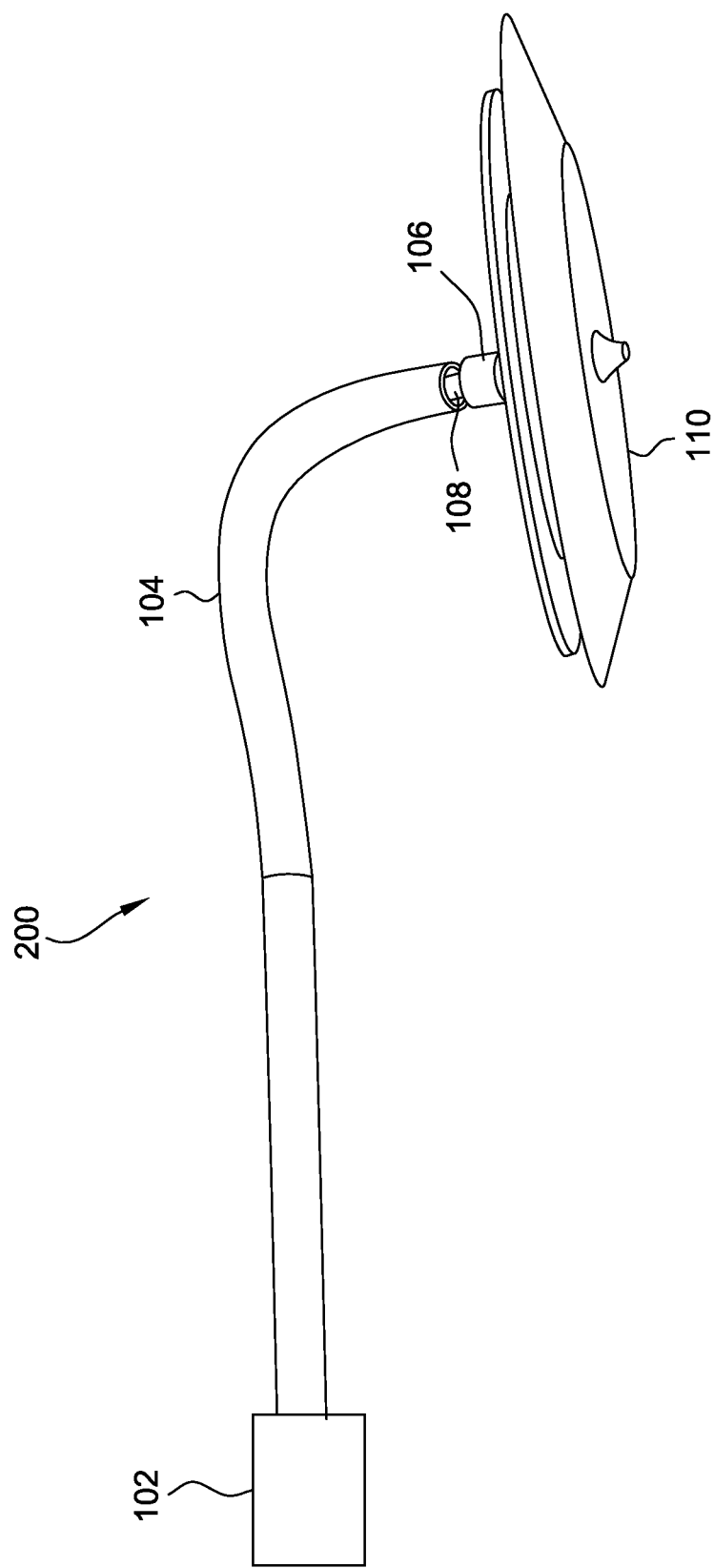
FIG. 2 is a schematic diagram of a delivery system in accordance with the present disclosure.

Turning now to FIG. 2, a schematic diagram of a delivery system 100 is shown. Delivery system 100 includes a delivery device 102 including a catheter 104 and a coupling member 106 configured to couple a distal end of a delivery cable 108 to a medical device 110 for facilitating the deployment of medical device 110 at a target site. Medical device 110 is deployed to treat the target site, and, in the example embodiment, is an occlusion device ("occluder").

Figure 3:
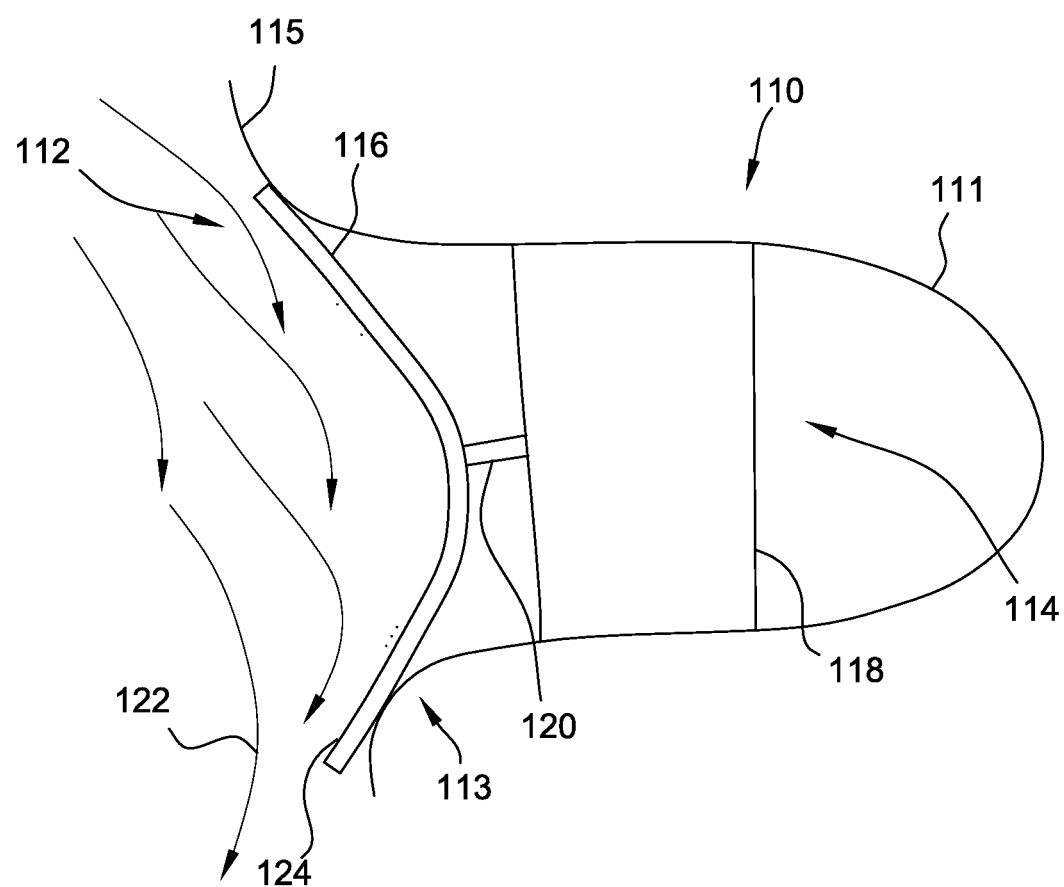
FIG. 3 is a schematic diagram of blood flow along or proximate to medical device in accordance with the present disclosure, when the medical device is deployed at a target site.

Turning now to FIG. 3, a schematic diagram of blood flow when medical device 110 according to the present disclosure is utilized for the occlusion of a target site 111 (e.g., an LAA) is shown. Medical device 110 includes a proximal end 112 and a distal end 114, wherein proximal end 112 includes a disc 116 and distal end 114 includes a lobe 118. Disc 116 is connected to lobe 118 by a connecting segment 120. When device 110 is deployed at the LAA 111, lobe 118 is positioned within the body of the LAA 111 and disc 116 is positioned at an opening 113 of the LAA 111. In the exemplary embodiment, disc 116 is formed with a three-dimensional shape, or having an appreciable depth, as described further herein, allowing for greater material apposition of disc 116 against tissue or walls 115 of the atrium around the opening 113 to the LAA 111, while maintaining a smooth transition between the walls 115 of the heart and disc 116. This increased material apposition decreases the risk of stagnant blood flow and ensures normal blood flow in a flow direction 122 proximate to disc 116 (e.g., along a proximal surface 124 thereof).

Figure 4:
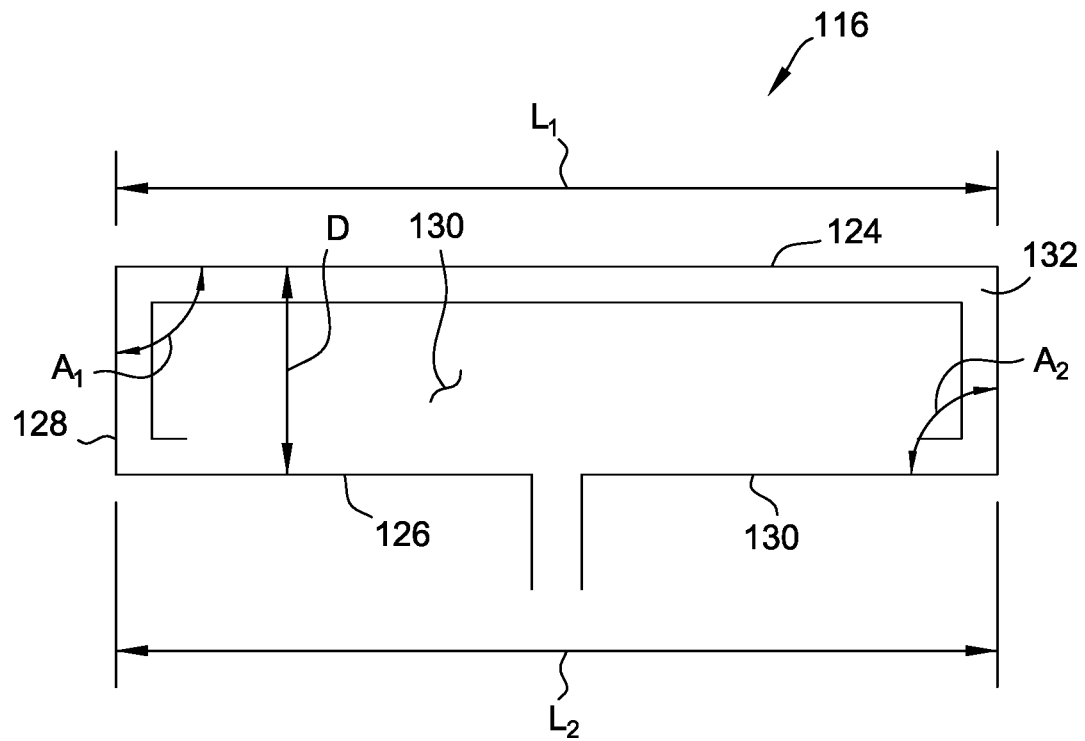
FIGS. 4-8 illustrate various exemplary embodiments of the medical device, including three-dimensional discs having various shapes and configurations.
Figure 5:
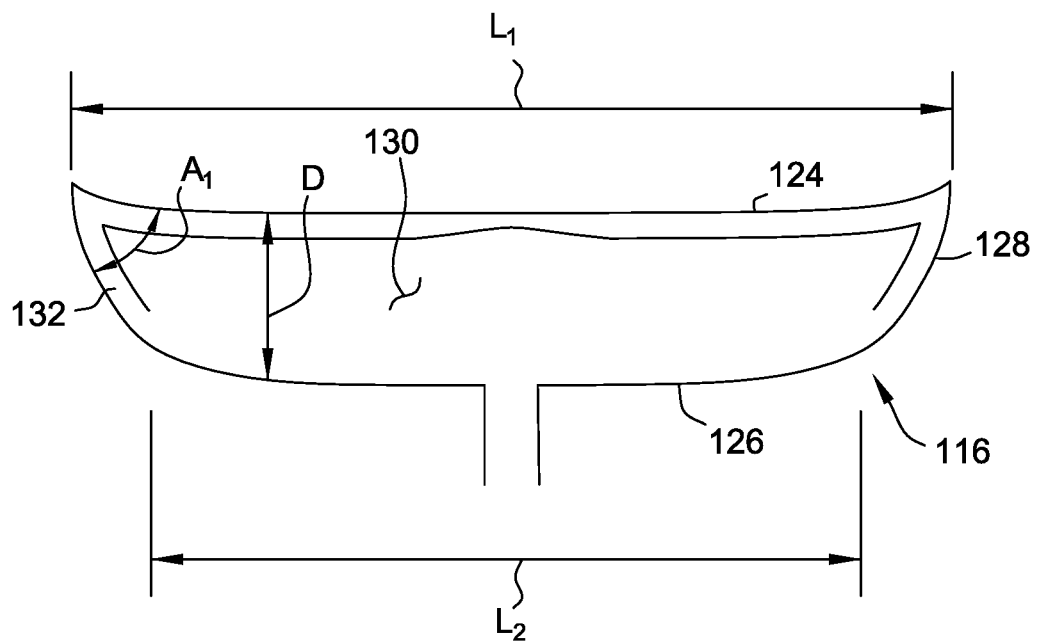
Figure 6:
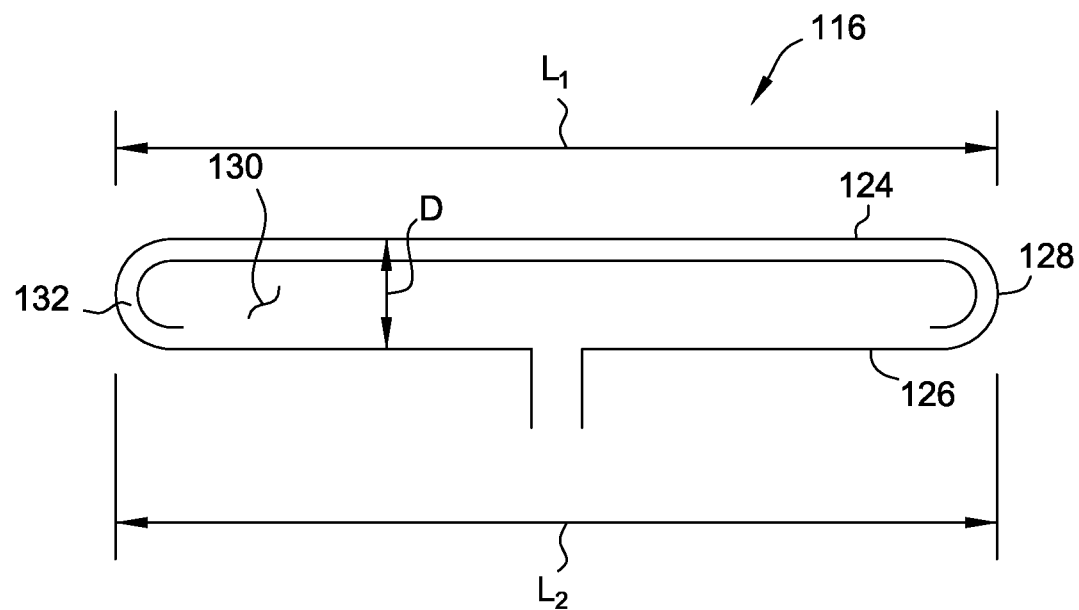
Figure 7:
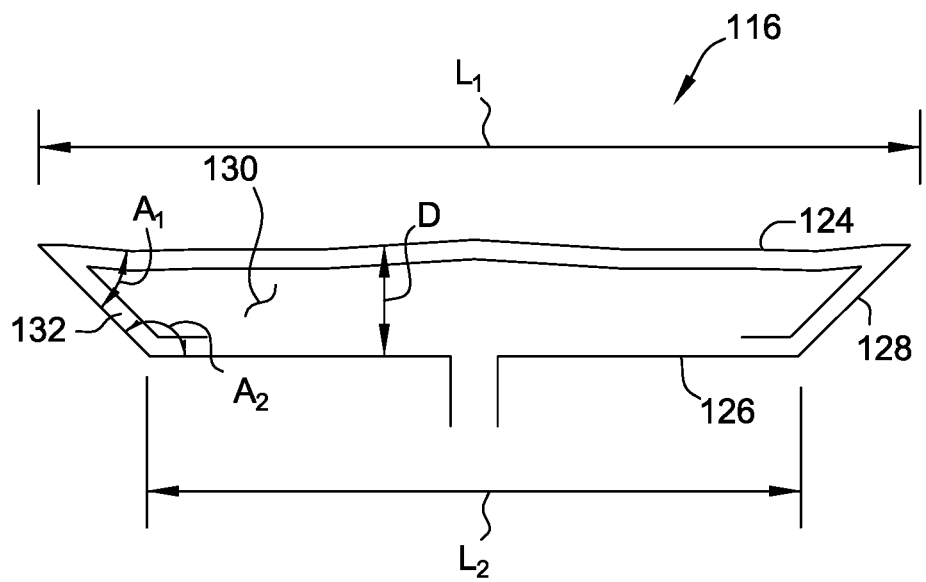

FIGS. 4-7 illustrate respective exemplary embodiments of disc 116 of medical device 110. In these embodiments, an entirety of disc 116 is three-dimensional in shape or has an appreciable depth. Specifically, FIG. 4 is a cross sectional view of disc 116 formed with a rectangular three-dimensional shape, FIG. 5 is a cross sectional view of disc 116 formed with a half-rounded (or partially rounded) three-dimensional shape, FIG. 6 is a cross sectional view of disc 116 formed with a fully rounded shape, and FIG. 7 is a cross sectional view of disc 116 formed with a trapezoidal three-dimensional shape.

As shown in FIGS. 4-7, disc 116 includes a proximal surface 124 having a first length (or diameter) $L_1$, a distal surface 126 having a second length (or diameter) $L_2$, and a central surface 128 (also referred to as an edge surface or edge). Central surface 128 extends between and connects proximal surface 124 and distal surface 126. A depth D of disc 116 is defined between proximal surface 124 and distal surface 126. In some embodiments, a length of central surface 128 corresponds to or defines depth D. In some embodiments, such as the embodiment of disc 116 shown in FIG. 4, depth D is defined consistently along the entirety of disc 116. In other embodiments, depth D varies along disc 116. Depth D may be 0.006 to 0.2 inches, more particularly 0.125 to 0.2 inches or 1 mm to 10 mm.

Proximal surface 124, distal surface 126, and central surface 128 define a cavity 130 of disc 116 therebetween. In the exemplary embodiment, disc 116 (and the rest of medical device 110) is formed from an occlusive fabric 132, and cavity 130 is defined between sheets of fabric 132 forming proximal surface 124 and distal surface 126 (which may be each be defined by a single layer or a double layer of fabric 132). That is, depth D represents a depth distance defined between these surfaces 124, 126 and by which surface 124, 126 are separated.

As shown in FIGS. 4 and 6, first length $L_1$ (or diameter) of proximal surface 124 may be approximately equal to second length $L_2$ (or diameter) of distal surface 126. As shown in FIGS. 5 and 7, first length $L_1$ of proximal surface 124 may be greater than second length $L_2$ of distal surface 126.

In some embodiments, central surface 128 extends linearly between proximal surface 124 and distal surface 126 (see, e.g., FIGS. 4 and 7). Central surface 128 may adjoin proximal surface 124 at an angle $A_1$. Angle $A_1$ may be approximately equal to a 90 degree angle or may be less than 90 degrees. Central surface 128 may adjoin distal surface 126 at an angle $A_2$. Angle $A_2$ may be greater than or equal to about 90 degrees.

Central surface 128 may alternatively adjoin proximal surface 124 and/or distal surface 126 with an angular or arcuate (e.g., curved) connection (see, e.g., FIGS. 5 and 6). It is also contemplated that central surface 128 may be curved between proximal surface 124 and distal surface 126 (see, e.g., FIGS. 5 and 6). Central surface 128 may have a radius of curvature. The radius of curvature may be in a range between 0.003 to 0.1 inches, more particularly 0.0625 to 0.1 inches or 2 mm to 10 mm. The radius of curvature may vary to ensure proper occlusive function and/or positioning of disc 116 within opening 113, while maintaining normal blood flow along or proximate to disc 116.

Figure 8:
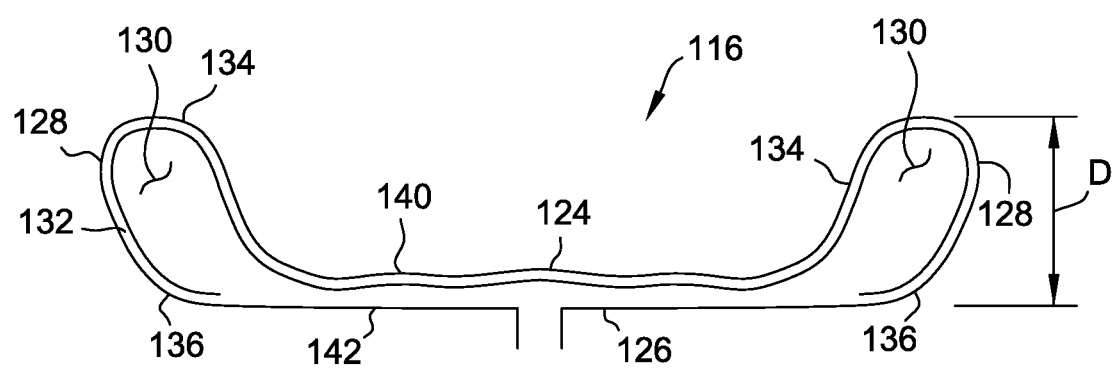

FIG. 8 illustrates another embodiment of disc 116 of medical device 110, in which portions of disc 116 are three-dimensional. Proximal surface 124 includes a proximal peripheral portion 134. Distal surface 126 includes a distal peripheral portion 136. Central surface 128 extends between and connects proximal peripheral portion 134 and distal peripheral portion 136. In some embodiments, proximal peripheral portion 134 and/or distal peripheral portion 136 extends in a proximal longitudinal direction.

In the embodiment of FIG. 8, cavity 130 is defined along the periphery of disc 116, as an annular cavity 130. That is, proximal surface 124 and distal surface 126 are spaced apart only along the periphery of disc 116. The depth distance D, defined between proximal surface 124 and distal surface 126 at peripheral portions 134, 136 thereof, provides a three-dimensional shape to the peripheral edges of disc 116. A central portion 140 of proximal surface 124, radially inward of peripheral portion 134, is directly adjacent to a central portion 142 of distal surface 126, radially inward of peripheral portion 136 (e.g., no cavity 130 is defined between surfaces 124, 126 in this central portion).

In one embodiment, medical device 110 is formed from a shape-memory material. One particular shape memory material that may be used is Nitinol. Nitinol alloys are highly elastic and are said to be "superelastic," or "pseudoelastic." This elasticity may allow medical device 110 to be resilient and return to a preset, expanded configuration for deployment following passage in a distorted form through delivery catheter 104. Further examples of materials and manufacturing methods for medical devices with shape memory properties are provided in U.S. Publication No. 2007/0265656 titled "Multi-layer Braided Structures for Occluding Vascular Defects" and filed on Jun. 21, 2007, which is incorporated by reference herein in its entirety.

It is also understood that medical device may be formed from various materials other than Nitinol that have elastic properties, such as stainless steel, trade named alloys such as Elgiloy®, or Hastalloy, Phynox®, MP35N, CoCrMo alloys, metal, polymers, or a mixture of metal(s) and polymer(s). Suitable polymers may include PET (Dacron™), polyester, polypropylene, polyethylene, HDPE, Pebax, nylon, polyurethane, silicone, PTFE, polyolefins and ePTFE. Additionally, it is contemplated that the medical device may comprise any material that has the desired elastic properties to ensure that the device may be deployed, function as an occluder, and be recaptured in a manner disclosed within this application.

In some embodiments, disc 116 is shaped as desired by heat-setting fabric 132 over a mandrel having a complementary shape. Additionally or alternatively, disc 116 may include a frame therein, where the frame has the desired final shape of disc 116. Fabric 132 may be coupled to this frame to form disc 116.

Figure 9:
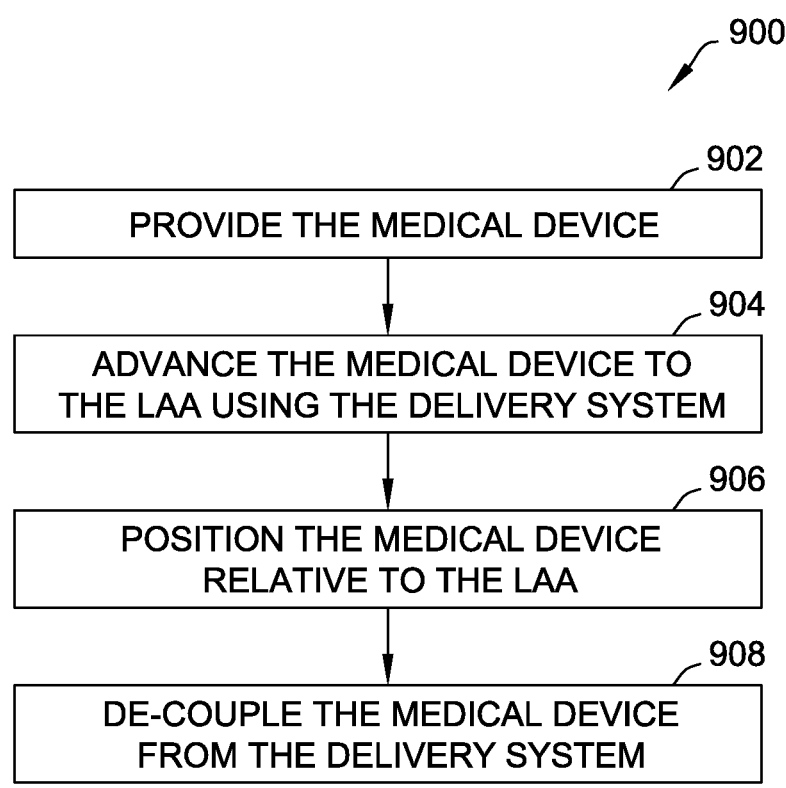
FIG. 9 is a flow diagram of a method of occluding a target site within a patient's vascular system with a device in accordance with the present disclosure.

Turning now to FIG. 9, a flow diagram of an exemplary method 900 of using medical device 110 to occlude an LAA in a patient is shown. In the exemplary embodiment, method 900 includes providing 902 a medical device. As described herein, the medical device includes a proximal end and a distal end, wherein the proximal end comprises a disc and the distal end comprises a lobe, wherein the disc and lobe are connected by a connecting member, wherein the disc comprises a proximal surface, a distal surface, and a central surface extending between and connecting the proximal surface and distal surface, wherein the central surface separates the proximal surface from the distal surface by a predetermined depth distance.

Method 900 also includes advancing 904 the medical device to the LAA using a delivery system including a catheter and a delivery cable, positioning 906 the medical device relative to the LAA to occlude blood flow to and from the LAA, and de-coupling 908 the medical device from the delivery cable to deploy the medical device Method 900 may include additional, alternative, and/or fewer steps, including those described herein. For example, in some embodiments, positioning 906 the medical device relative to the LAA includes placing the lobe of the medical device within the body of the LAA and the disc outside of the LAA to abut the adjacent wall surrounding the opening of the LAA.

Additionally, de-coupling 908 the medical device from the delivery cable includes transitioning the medical device from the constricted configuration adopted for delivery from a catheter to the preset expanded configuration.

While embodiments of the present disclosure have been described, it should be understood that various changes, adaptations and modifications may be made therein without departing from the spirit of the disclosure and the scope of the appended claims. Further, all directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. It is intended that all matter contained in the above description or shown in the accompanying drawings shall be interpreted as illustrative only and not limiting. Changes in detail or structure may be made without departing from the spirit of the disclosure as defined in the appended claims.

Many modifications and other embodiments of the disclosure set forth herein will come to mind to one skilled in the art to which this disclosure pertains having the benefit of the teachings presented in the foregoing descriptions and the associated drawings. Therefore, it is to be understood that the disclosure is not to be limited to the specific embodiments described and that modifications and other embodiments are intended to be included within the scope of the appended claims. Although specific terms are employed herein, they are used in a generic and descriptive sense only and not for purposes of limitation.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A medical device for treating a target site, the medical device comprising:
 a proximal end and a distal end, wherein the proximal end comprises a disc and the distal end comprises a lobe, wherein the disc and lobe are spaced from one another and connected by a connecting member, wherein the lobe is configured to be positioned within a defect at the target site and the disc is configured to be positioned against and cover an opening to the defect when the medical device is deployed at the target site,
 wherein the disc comprises a proximal surface, a distal surface, and a central surface extending between and connecting the proximal surface and distal surface, wherein the central surface separates the proximal surface from the distal surface by a predetermined depth distance such that an enclosed cavity is defined between the proximal surface and the distal surface, wherein the central surface has a radius of curvature, the predetermined depth distance and the radius of curvature cooperatively defining a three-dimensional shape of the disc that facilitates improved apposition of the disc against tissue at the opening to the defect at the target site,
 wherein the predetermined depth distance is between 0.125 and 0.2 inches and the radius of curvature is between 0.0625 and 0.1 inches.

2. The medical device of claim 1, wherein the proximal surface has a first length and the distal surface has a second length.

3. The medical device of claim 2, wherein the first length of the proximal surface is approximately equal to the second length of the distal surface.

4. The medical device of claim 2, wherein the first length of the proximal surface is greater than the second length of the distal surface.

5. The medical device of claim 1, wherein the central surface separates the proximal surface from the distal surface adjacent a peripheral edge of the disc.

6. The medical device of claim 5, wherein a central portion of the proximal surface radially inward of the peripheral edge is directly adjacent to a central portion of the distal surface such that no cavity is defined between the central portion of the proximal surface and the central portion of the distal surface.

7. The medical device of claim 1, wherein the medical device is formed from a braided shape-memory or elastic material.

8. The medical device of claim 7, wherein the material is selected from nitinol, stainless steel, MP35N, a shape-memory or elastic polymeric material, and combinations thereof.

9. The medical device of claim 1, wherein the disc includes more than one layer of a braided shape-memory material.

10. The medical device of claim 9, wherein each of the distal surface and the proximal surface comprises two layers of the braided shape-memory material.

11. The medical device of claim 9, wherein the more than one layer of the braided shape memory material improves retention of the disc against the tissue at the opening to the defect at the target site.

12. A delivery system for deploying a medical device to a target site, the delivery system comprising:
 a medical device comprising:
  a proximal end and a distal end, wherein the proximal end comprises a disc and the distal end comprises a lobe, wherein the disc and lobe are spaced from one another and connected by a connecting member, and wherein the lobe is configured to be positioned within a defect at the target site and the disc is configured to be positioned against and cover an opening to the defect when the medical device is deployed at the target site, wherein the disc comprises a proximal surface, a distal surface, and a central surface extending between and connecting the proximal surface and distal surface, wherein the central surface separates the proximal surface from the distal surface by a predetermined depth distance such that an enclosed cavity is defined between the proximal surface and the distal surface, wherein the central surface has a radius of curvature, the predetermined depth distance and the radius of curvature cooperatively defining a three-dimensional shape of the disc that facilitates improved apposition of the disc against tissue at the opening to the defect at the target site, wherein the predetermined depth distance is between 0.125 and 0.2 inches and the radius of curvature is between 0.0625 and 0.1 inches; and a delivery device comprising:
  a delivery catheter;
  a delivery cable within the delivery catheter and translatable with respect to the delivery catheter; and
  a coupling member configured to couple the medical device to the delivery cable for facilitating at least one deployment of the medical device at the target site.

13. A method for treating a target site including a left atrial appendage (LAA), the method comprising:
  providing a medical device comprising a proximal end and a distal end, wherein the proximal end comprises a disc and the distal end comprises a lobe, wherein the disc and lobe are spaced from one another and connected by a connecting member, and wherein the lobe is configured to be positioned within the LAA at the target site and the disc is configured to be positioned against and cover an opening to the LAA when the medical device is deployed, wherein the disc comprises a proximal surface, a distal surface, and a central surface extending between and connecting the proximal surface and distal surface, wherein the central surface separates the proximal surface from the distal surface by a predetermined depth distance such that an enclosed cavity is defined between the proximal surface and the distal surface, wherein the central surface has a radius of curvature, the predetermined depth distance and the radius of curvature cooperatively defining a three-dimensional shape of the disc that facilitates improved apposition of the disc against tissue at the opening to the LAA, wherein the predetermined depth distance is between 0.125 and 0.2 inches and the radius of curvature is between 0.0625 and 0.1 inches;
  advancing the medical device to the LAA using a delivery system including a catheter and a delivery cable;
  positioning the medical device relative to the LAA to occlude blood flow; and
  de-coupling the medical device from the delivery cable to deploy the medical device.

14. The method according to claim 13, wherein positioning the medical device comprises placing the lobe of the medical device within a body of the LAA and the disc outside of the LAA to abut an adjacent wall surrounding the opening of the LAA.

15. The method according to claim 13, wherein positioning the medical device comprises transitioning the medical device from a constricted configuration adopted for delivery through the catheter to an expanded configuration.

16. The method according to claim 15, where positioning the medical device further comprises:
  advancing the lobe distally from the catheter into a body of the LAA, wherein said advancing comprises transitioning the lobe from the constricted configuration to the expanded configuration;
  retracting the catheter proximally; and
  positioning the disc outside of the LAA and abutting a wall surrounding the opening of the LAA, wherein said positioning comprises transitioning the disc from the constricted configuration to the expanded configuration.

\* \* \* \* \*